(12) United States Patent
Jovancicevic et al.

(10) Patent No.: US 9,726,594 B2
(45) Date of Patent: Aug. 8, 2017

(54) ELECTROCHEMICAL SENSOR FOR MONITORING UNDER-DEPOSIT CORROSION

(71) Applicant: Baker Hughes Incorporated, Houston, TX (US)

(72) Inventors: Vladimir Jovancicevic, Richmond, TX (US); Sunder Ramachandran, Sugar Land, TX (US); Carlos M. Menendez, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 146 days.

(21) Appl. No.: 14/546,442

(22) Filed: Nov. 18, 2014

(65) Prior Publication Data
US 2016/0139030 A1 May 19, 2016

(51) Int. Cl.
*G01N 17/02* (2006.01)

(52) U.S. Cl.
CPC .................. *G01N 17/02* (2013.01)

(58) Field of Classification Search
CPC ......... G01N 17/02; G01N 17/00; G01N 27/20
See application file for complete search history.

(56) References Cited

U.S. PATENT DOCUMENTS

| | | | |
|---|---|---|---|
| 4,098,662 A | 7/1978 | Schell et al. | |
| 4,196,057 A | 4/1980 | Laurence et al. | |
| 4,587,479 A * | 5/1986 | Rhoades | G01N 17/00 324/700 |
| 4,863,572 A * | 9/1989 | Jasinski | G01N 17/02 204/404 |
| 5,188,715 A * | 2/1993 | Chen | G01N 17/02 204/404 |
| 6,280,603 B1 | 8/2001 | Jovancicevic | |
| 6,880,402 B1 | 4/2005 | Couet et al. | |
| 7,368,050 B2 | 5/2008 | Jovancicevic et al. | |
| 7,622,030 B2 | 11/2009 | Gill et al. | |
| 7,686,938 B2 | 3/2010 | Gill et al. | |
| 7,695,601 B2 * | 4/2010 | Jiang | G01N 27/403 204/400 |
| 7,713,405 B2 | 5/2010 | Jovancicevic et al. | |
| 8,109,161 B2 | 2/2012 | Jovancicevic et al. | |
| 8,133,383 B2 | 3/2012 | Hammonds et al. | |

(Continued)

OTHER PUBLICATIONS

Horsup, D.I., et al., , Breakthrough Corrosion Inhibitor Technology for Heavily Fouled Systems; Corrosion vol. 65, No. 8, p. 527-544 (2009).

(Continued)

*Primary Examiner* — Jermele M Hollington
*Assistant Examiner* — Alvaro Fortich
(74) *Attorney, Agent, or Firm* — Mossman, Kumar & Tyler, P.C.

(57) ABSTRACT

An under-deposit corrosion (UDC) sensor includes a probe body with a curved concave probe surface that may have pre-deposited or in-situ formed thereon a material that accelerates the process of under deposit corrosion. The UDC sensor uses electrochemically-based localized monitoring techniques for assessing under-deposit pitting corrosion and the effectiveness of chemical treatment programs that mitigate under-deposit corrosion in well tubing, pipelines, vessels, and/or tanks.

19 Claims, 4 Drawing Sheets

(56) References Cited

U.S. PATENT DOCUMENTS

| | | | |
|---|---|---|---|
| 8,461,946 B1* | 6/2013 | Tsironis | G01R 1/26 333/17.3 |
| 2002/0078752 A1* | 6/2002 | Braunling | G01N 17/04 73/627 |
| 2003/0132144 A1* | 7/2003 | Herbert-Guillou | G01N 17/02 210/86 |
| 2005/0274628 A1* | 12/2005 | Yang | G01N 17/02 205/775.5 |
| 2006/0006353 A1* | 1/2006 | Wirthlin | G01F 23/2922 250/573 |
| 2006/0132885 A1* | 6/2006 | Pichot | G02F 1/155 359/265 |
| 2007/0261958 A1* | 11/2007 | Jiang | G01N 27/403 204/400 |
| 2008/0134770 A1 | 6/2008 | Horsup | |
| 2008/0141780 A1* | 6/2008 | Wavering | G01N 17/04 73/723 |
| 2009/0173629 A1* | 7/2009 | Kidwell | G01N 27/3335 204/415 |
| 2009/0308753 A1* | 12/2009 | Wong | B82Y 30/00 205/50 |
| 2010/0108566 A1* | 5/2010 | Scattergood | C10G 7/10 208/47 |
| 2011/0267074 A1* | 11/2011 | Xie | G01N 33/2823 324/629 |

OTHER PUBLICATIONS

Stewart, S. et al., "Evaluation of a New Sour Gas Corrosion Inhibitor for Field Application via Local Corrosion Monitoring Techniques", Paper No. 10274, Corrosion 2010, NACE International.

Moloney, J., et al., "In Situ Assessment of Pitting Corrosion and its Inhibition Using a Localized Monitoring Technique" Corrosion, vol. 66, No. 6, p. 110-118, Jun. 2010, NACE International.

Menendez, C.M., et al., "New Method for Assessing Corrosion Under Iron Sulfide Deposits and C02/H2S Conditions", Paper No. 11265, Corrosion 2011, NACE International.

Roth, G., et al., "Improving Throughput and Integrity Management at Water Injection Facilities by Chemically Reducing Deposits", Paper No. 23 presented at 2011 Northern Nace Western Conference, Feb. 6-8, 2011 at Regina, Saskatchewan, Canada, NACE International.

* cited by examiner

ELECTROCHEMICAL SENSOR FOR MONITORING UNDER-DEPOSIT CORROSION

TECHNICAL FIELD

The invention relates to devices and methods for monitoring the corrosion of metals, and, in one non-limiting aspect, more particularly relates to devices and methods for monitoring the under-deposit corrosion of metals in tubing, pipelines, vessels and/or tanks.

TECHNICAL BACKGROUND

Under-deposit corrosion (UDC) is a serious problem in oil and gas transmissions lines, tubing, tanks, and separation vessels worldwide that has had a serious impact on pipeline operations and production, and health, safety and environment (HS&E) compliance. Despite the fact that this has been a persistent problem in the industry, there has been little work conducted towards development of a reliable monitoring method for UDC.

UDC is sometimes called "cell corrosion", and is typically very aggressive and localized, causing deep penetration of the metal surface with lesser general corrosion in the surrounding areas. Due to surface deposits, electrical imbalance or some other initiating mechanism, all corrosion factors attack a select number of individual sites. In some cases, pitting is extended throughout the entire metal surface, giving it an irregular or very rough surface profile. In other instances, pits are concentrated in specific areas, leaving the majority of the metal surface in like-new condition. Galvanized pipe is particularly highly susceptible to UDC.

It is difficult to build a probe where one can ensure that localized corrosion occurs. It would be advantageous if a new sensor or probe were discovered that would be an improvement over the presently known probes and methods for monitoring UDC.

SUMMARY

There is provided, in one non-limiting embodiment, an under-deposit corrosion (UDC) sensor that includes a probe body; a curved concave probe surface of constant radius R comprising at least one reference electrode surface, at least one working electrode surface, and at least one counter electrode surface; where the respective electrode surfaces are electrically insulated one from each other. The UDC sensor further includes a porous, electrically insulating layer over the at least one reference electrode surface and the at least one counter electrode surface, which porous, electrically insulating layer conducts ions therethrough. There is no porous, electrically insulating layer over the at least one working electrode surface. An electrically conductive lead is electrically attached to each respective electrode surface.

In an alternate non-limiting embodiment there is provided a system for online monitoring under-deposit corrosion in real time which system includes a structure having a concave, curved bottom surface of radius R, where the structure is selected from the group consisting of a pipeline, a tubing, a conduit, a vessel, a container, and/or a tank. The system further includes a UDC sensor that comprises a probe body; a curved concave probe surface of constant radius R comprising at least one reference electrode surface, at least one working electrode surface, and at least one counter electrode surface; where the respective electrode surfaces are electrically insulated one from each other. The UDC sensor further includes a porous, electrically insulating layer over the at least one reference electrode surface and the at least one counter electrode surface, which porous, electrically insulating layer conducts ions therethrough. There is no porous, electrically insulating layer over the at least one working electrode surface. The UDC sensor also comprises an electrically conductive lead electrically attached to each respective electrode surface. The system also includes a machine electrically connected to and configured to receive measurements from the electrically conductive leads, and further configured to measure and/or analyze the measurements for data selected from the group consisting of changes in electrical potential, linear polarization resistance, localized corrosion rate, electrical charge, and combinations thereof. The under-deposit corrosion sensor is mounted in the bottom of the structure so that the curved concave probe surface is flush with the concave, curved bottom surface of the structure.

Further in another non-restrictive version, there is provided a method for measuring under-deposit corrosion, where the method includes utilizing a system for monitoring under-deposit corrosion in real time as described in the previous paragraph. The method involves measuring and/or analyzing the measurements for data selected from the group consisting of changes in electrical potential, linear polarization resistance, localized corrosion rate, electrical charge, and combinations thereof.

BRIEF DESCRIPTION OF THE DRAWING

FIGS. 7A-7D illustrate top and cross-sectional perspective views of another non-limiting embodiment of the under-deposit corrosion sensor configured to fit into the bottom of a conventional, cylindrical pipe, where the concave probe surface has a roughly rectangular or "dog tag"-like shape, where FIGS. 7C and 7D are cross-sectional perspective views and FIGS. 7A and 7B are top views thereof, respectively, and where FIGS. 7A and 7B do not have a deposit on the working electrode and FIGS. 7B and 7D have a deposit on the working electrode.

It should be appreciated that the Figures are not necessarily to scale, and that certain features may be exaggerated or may not be in proportion for purposes of illustration, and the invention is not necessarily so limited.

DETAILED DESCRIPTION

A novel under-deposit corrosion (UDC) sensor has been discovered that may use electrochemical monitoring techniques for assessing UDC and the effectiveness of chemical treatment programs that prevent, inhibit or mitigate UDC in common places where it occurs such as metal tubing, pipelines, vessels, tanks and the like. The probe also uses localized monitoring techniques which allow for rapid detection of the pitting corrosion. This UDC probe will help operators meet their goal of reducing the UDC throughout the field and improve operational efficiency by providing better monitoring and control of UDC.

Operation of the UDC sensor involves the in-situ or pre-deposited layer of a deposit under which corrosion is expected or likely to occur. In one non-limiting embodiment, the size of the probe with the curvature of constant radius (R, see FIG. 6), such as to result in a deposit over a curvature (an angle or arc A of 1-120°; again see FIG. 6) necessary to obtain a 0.01 mm-1 cm thick deposit, which thickness will vary depending on the size of the UDC probe relative to the actual pipe diameter (D) to be monitored. The deposited material may be from an actual pipe that is pre-deposited or formed in situ on the electrochemical probe where UDC occurs.

The probe described herein will allow for the electrochemical monitoring of localized corrosion and will draw upon previous work on localized corrosion monitoring. Unlike the probe described herein, the probe of U.S. Patent Application 2008/0134770 does not have the ability for direct under-deposit corrosion measurement; instead, the deposit removal probe of this published patent application monitors the effectiveness of a chemical at removing deposits from the internal surface of a pipeline used to transport fluids, which probe comprises a chamber constructed from mesh having a pore size sufficient to retain a sample of said deposit in said chamber while also allowing the deposit to be removed from the chamber with the action of the chemical and liquid flow through the pipeline and methods of using the probe to determine the effectiveness of a chemical at removing deposits from the internal surface of a pipeline and monitor corrosion rates of surfaces in contact with the deposit and in the bulk fluid.

The probe described herein provides a method of collecting data and measurement as part of a unique electrochemical method for monitoring UDC by using a special design feature such as pipe curvature to ensure that the UDC occurs over an extended surface area. Pitting corrosion is measured using an appropriate localized corrosion method that will record localized corrosion events in real time. The device of U.S. Patent Application 2008/0134770 cannot do this.

There is no alternative method currently available utilizing a probe for monitoring UDC. Other methods that employ probes for general corrosion (e.g. linear polarization resistance (LPR), electrical resistance (ER)) include microscopic examination of coupon surfaces. Additional ways for monitoring pipeline corrosion include various inspection methods that typically involve techniques such as ultrasound, magnetic flux or eddy current. These methods are difficult to utilize for non-piggable pipelines. A "non-piggable" pipeline is one that cannot be traversed by a "pig", that is a device with blades or brushes inserted into a pipeline for travelling a length thereof for cleaning purposes, or which may have other equipment or instrumentation to gather data. The method using the UDC probe described herein will allow for quick detection of localized corrosion in situ.

One suitable manner of measuring UDC is to utilize the UDC probe described herein in a pipe line application, especially in piggable pipelines. Various embodiments of the UDC sensor are schematically outlined in FIGS. 1-7 as will be described in more detail below. One feature of the UDC sensor or probe is that it uses electrochemistry to monitor under-deposit corrosion. Another feature of the UDC probe is the presence of a curvature corresponding to pipe diameter in which it is installed so that it may measure UDC below an actual deposit in the pipeline or other structure (e.g. a tubing, a conduit, a pipeline, a vessel, a tank, a container, and other process equipment).

An advantage of the UDC sensor and its method of use is that the deposited material that creates UDC is deposited in-situ on the probe. UDC deposit materials include, but are not necessarily limited to, ferrous sulfide (iron sulfide or FeS), ferrous oxide (FeO), ferrous carbonate ($FeCO_3$), silicate, and combinations thereof. These deposits may also include, and typically include, organic material which may include, but not necessarily be limited to, asphaltenes, paraffins, bio-films, and combinations thereof. Of course, water is also typically a component of these deposits.

Using the appropriate pre-deposited material or in situ-formed deposit with the UDC sensor described herein ensures that localized corrosion will occur on the probe. The probe directly measures the under-deposit corrosion and provides a method of assessing the effectiveness of a chemical treatment applied, for instance the continuous, intermittent or regular introduction of a corrosion inhibitor. The UDC sensor is intended for applications in pipelines and process vessels where stagnant flow causes under-deposit corrosion in the oil and gas industry. While the method is particularly suitable for the oil and gas industry, there are a number of other industries such as petroleum refining and petrochemicals and water treatment where under-deposit corrosion also occurs and this method and probe can be used for these industries.

Figure 1:
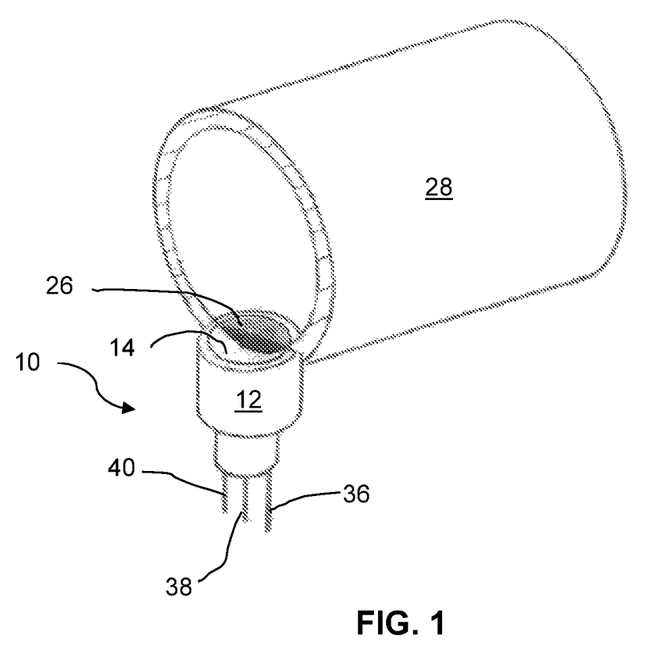
FIG. 1 is a cross-sectional perspective view of a short section of pipe having the under-deposit corrosion sensor mounted on the bottom thereof illustrating how the deposit in the pipe is formed in the curved concave probe surface.
Figure 2:
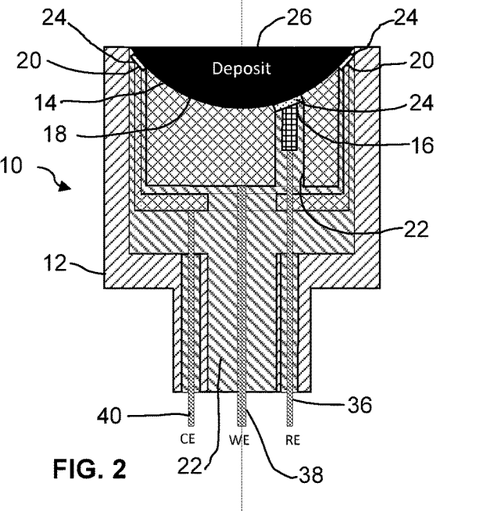
FIG. 2 is a cross-sectional, side profile view of another non-limiting embodiment of the under-deposit corrosion sensor viewed in a direction parallel to a pipe; although a pipe is not shown.
Figure 6:
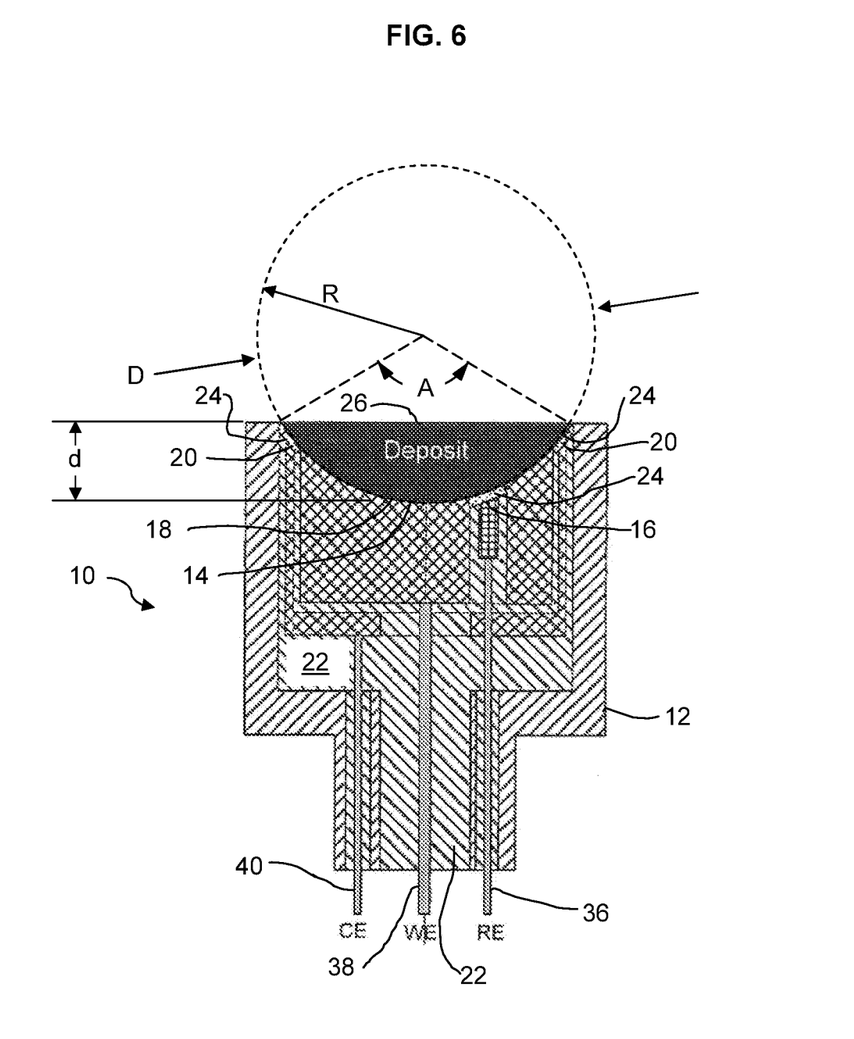
FIG. 6 is a cross-sectional, side profile view of the under-deposit corrosion sensor of FIG. 1 showing an outline of the inner diameter of a pipe under which the sensor may be monitored, where the radius (R) and diameter (D) of the pipe are schematically illustrated, as well as the arc or angle (A) of the deposit within the cross-section of the pipe and the depth (d) of the deposit.

In more detail, FIGS. 2 and 6 illustrate a cross-sectional, side profile view of one non-limiting embodiment of a under-deposit corrosion sensor 10 that has a probe body 12 with a curved concave probe surface 14 on the top thereof (in the orientation of FIG. 1) which has a constant radius R (see FIG. 6) The curved concave probe surface 14 has a reference electrode (RE) surface 16, a working electrode (WE) surface 18 and a counter electrode (CE) surface 20. The respective electrode surfaces are electrically insulated one from each other with any suitable electrically insulating material 22, including, but not necessarily limited to plastic, ionic membranes, glass frits, or other ionically conductive materials or ionically conductive films and combinations thereof. There is an electrically insulating, porous layer 24 over the electrode surfaces 16 and 20, which electrically insulating, porous layer conducts ions therethrough, which may be any suitable film or membrane including, but not necessarily limited to, a glass frit, ionic crystals, solid electrolytes and combinations of these. Note that there is no porous, electrically insulating layer 24 over WE surface 18.

The WE surface 18 may be relatively large compared to the smaller RE surface 16, and may be made of carbon steel, including, but not necessarily limited to C1018, X65, C1010 and the like. In one non-limiting embodiment, the material of the WE surface 18 may be similar or identical to the material of the pipe 28 or vessel or other structure in which it is mounted. The pre-formed or pre-deposited deposit or in situ-formed deposit 26 is deposited on the WE surface 18. The deposited material 26 is of a given thickness and may be generally flush with the pipe surface; see also FIGS. 1, 2 and 6.

Figure 5:
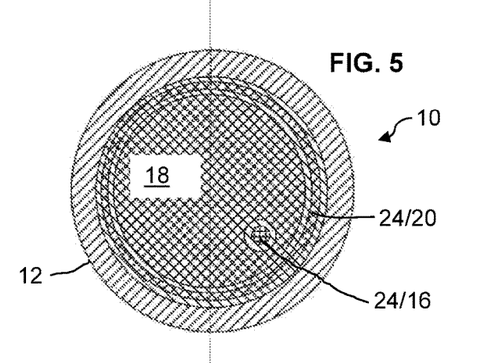
FIG. 5 is a top plan view of the under-deposit corrosion sensor of FIG. 2 that shows no deposit in the curved concave probe surface, where the footprint of the under-deposit corrosion sensor is circular.

The WE surface 18 is separated from the counter electrode surface 20, shown as the outer-most electrode, by any suitable insulating material 22, as previously described. The CE surface 20 is exposed to water and is separated from under-deposit material 26 by means of a suitable porous, electrically insulating material, e.g. a glass frit 24. In FIG. 5, which is a top-down or plan view of the UDC sensor 10 of FIGS. 1 and 2, the porous, electrically insulating layer 24 covering the CE electrode 20 is noted as 24/20 and the porous, electrically insulating layer covering the RE electrode 16 is noted as 24/16.

It will be appreciated that the geometric configuration of the RE 16, WE 18 and CE 20 need not be as shown in FIG. 5 or 7, but may have different shapes, relative sizes, and relative positions from those shown. It is expected that the UDC sensor 10 will work best when the WE 18 has a relatively larger surface area compared to the RE 16 and the CE 20. It is also expected that the UDC sensor 10 will work best when RE 16 is positioned within the shape of the WE 18, which in turn is positioned within the shape of CE 20, although other relative positions may be found to work.

The under-deposit corrosion sensor 10 also has electrically conductive leads 36, 38 and 40 electrically attached to each respective electrode surface 16, 18 and 20. These leads 36, 38 and 40 are connected to a machine that is configured to receive measurements from the electrically conductive leads, and further configured to measure and/or analyze the measurements for data selected from the group consisting of changes in electrical potential, linear polarization resistance (LPR), localized corrosion rate, electrical resistance (ER), electrical charge, and combinations thereof. The machine may be any device known in the art to take measurements and provide analysis of corrosion events, such as those described in one or more of the following issued US Patents assigned to Baker Hughes Incorporated:

U.S. Pat. No. 6,280,603—Electrochemical Noise Technique for Corrosion, V. Jovancicevic;
U.S. Pat. No. 7,368,050—Quantitative Transient Analysis of Localized Corrosion, V. Jovancicevic, W. Y. Mok, C. M. Menendez and P. Hammonds, 2008;
U.S. Pat. No. 7,622,030—General and Localized Corrosion Rate Measurements, R. P. Gill, V. Jovancicevic, W Y. Mok and P. Hammonds, 2009;
U.S. Pat. No. 7,686,938—Quantitative, Real Time Measurements of Localized Corrosion Events, R. P. Gill, V. Jovancicevic, W. Y. Mok and P. Hammonds, 2010;
U.S. Pat. No. 7,713,405—Quantitative Transient Analysis of Localized Corrosion, V. Jovancicevic, C. M. Menendez, P. Hammonds and W Y. Mok, 2010;
U.S. Pat. No. 8,133,383—Localized Corrosion Monitoring Device for Limited Conductivity Fluids, P. Hammonds and V. Jovancicevic, 2012.

All of these patents are incorporated herein in their entirety by reference.

FIG. 1 is a cross-sectional perspective view of a short length of pipe 28 having the under-deposit corrosion sensor 10 mounted on the bottom thereof illustrating how the deposit 26 in the pipe 28 is formed in the curved concave probe surface 14. The radius R of the curved concave probe surface 14 may be the same as the inner radius R or half of the inner diameter D of pipe 28, as more clearly shown in FIG. 6. Because these radii are the same and because the UDC sensor 10 is mounted in the bottom of the structure 28 so that the curved concave probe surface 14 is flush with the concave, curved bottom surface of the structure or pipe 28, the data and measurements collected are much more accurate. It will be appreciated that the size of the UDC sensor 10 shown in FIG. 1 is relatively larger compared to the diameter of the pipe 28 than would likely normally be the case for a commercial embodiment of a UDC sensor, but the relative size is exaggerated for clarity.

Figure 4:
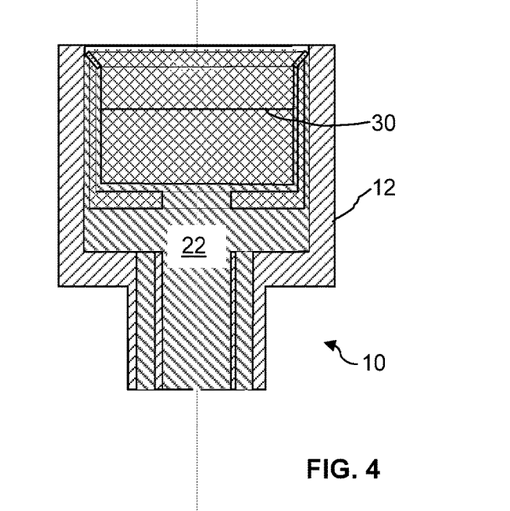
FIG. 4 is a cross-sectional, side profile view of the embodiment of the under-deposit corrosion sensor of FIG. 7 viewed in a direction perpendicular to a pipe; although a pipe is not shown.
Figure 7A:
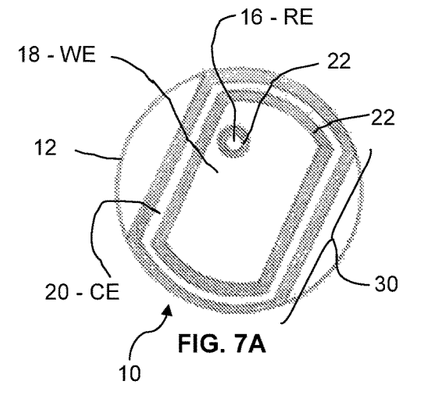
Figure 7B:
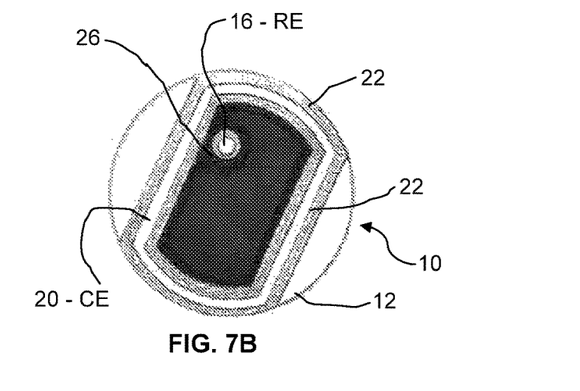
Figure 7C:
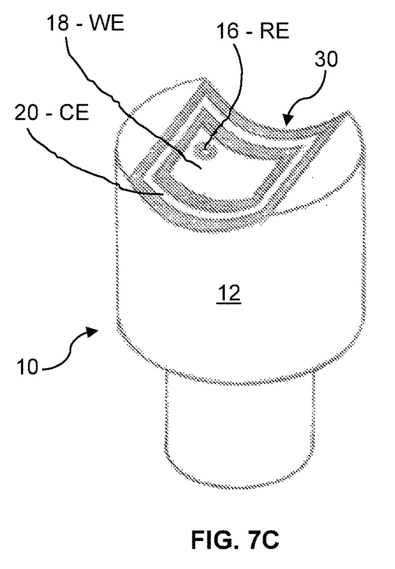
Figure 7D:
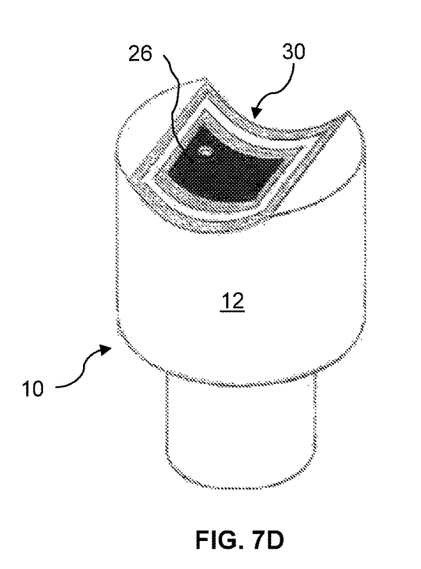

In the non-limiting embodiment shown in FIGS. 1 and 6, the curved concave probe surface 14 has a shape that is a partial cylinder, that is, if a cylinder is imagined lying on its curved side on a horizontal surface, and a horizontal slice is taken from the lower-most portion of the cylinder. This would be the shape of the deposit 26 if it were removed from FIGS. 1 and 6. This shape may also be seen with respect to the non-limiting embodiment shown in FIG. 7, where curved concave probe surface 30 has a "dog tag" like shape or roughly rectangular shape with curved ends. The same reference numerals are used for other parts of the probe 10, although they may have different shapes from other embodiments described and shown herein. FIGS. 7C and 7D are cross-sectional perspective views that illustrate how probe surface 30 that is curved in the pipeline circumference direction but straight along the axis of the pipeline would appear. FIGS. 7A and 7B are top views thereof, respectively. FIGS. 7A and 7B do not have a deposit on the WE 18, whereas FIGS. 7B and 7D illustrate a deposit 26 on the WE 18 in each Figure. FIG. 4 is a cross-sectional, side profile view of the embodiment of the under-deposit corrosion sensor of FIG. 7 viewed in a direction perpendicular to a pipe; although a pipe is not shown. The bottom of curved concave probe surface 30 would appear as a straight horizontal line, as shown.

Figure 3:
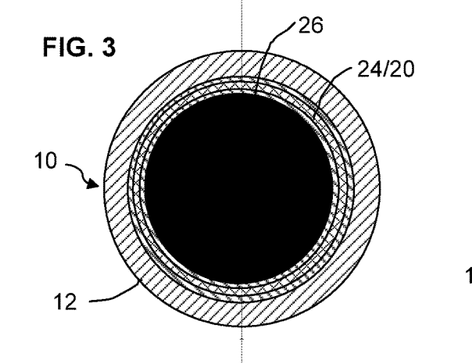
FIG. 3 is a top plan view of the under-deposit corrosion sensor of FIG. 2 showing a deposit in the curved concave probe surface, where the footprint of the under-deposit corrosion sensor is circular.

Shown in FIGS. 2, 3 and 5 is a different non-limiting embodiment of the UDC sensor 10. FIG. 2 is a cross-sectional, side profile view of another non-limiting embodiment of the under-deposit corrosion sensor 10 viewed in a direction parallel to a pipe, although a pipe is not shown; whereas FIG. 3 is a top plan view of the under-deposit corrosion sensor 10 of FIG. 2 showing a deposit 26 in the curved concave probe surface 14, where the footprint of the under-deposit corrosion sensor is 10 circular. Unlike the embodiment of UDC sensor 10 in FIGS. 4 and 7, in this embodiment the curved concave probe surface 14 is circular and has a shape that is a partial sphere. For instance, if a sphere rested on a horizontal surface had the horizontal slice taken from the bottom thereof the resulting shape would be that of deposit 16 in FIGS. 2 and 3. In other words, if deposit 26 was removed from FIGS. 2 and 3, it would have an "inverted dome"-shape.

The embodiments of the UDC sensor 10 shown in all of the Figures would be suitable for use in a flat-bottomed tank or vessel or other structure where there is likely to be stagnant flow of the fluid in the structure.

The pre-formed deposit or in situ-formed deposit 26 may have a thickness ranging from about 0.01 mm independently to about 1 cm; alternatively ranging from about 0.05 mm independently to about 1 mm. Where the term "independently" is used with respect to a range, it means that any lower threshold may be used together with any upper threshold to form a suitable alternative range. It will be further appreciated that the deposit thickness is independent of the curvature, that is the radius R or diameter D.

Many modifications may be made in the present invention without departing from the spirit and scope thereof that are defined only by the appended claims. For example, certain elements or features per se, or combinations of elements or features thereof other than those specifically set out herein may be found by one of routine skill in the art to be particularly advantageous, in non-limiting instances, different dimensions, positions, relative sizes, metal compositions, deposit components and compositions, electrodes, porous layers, curved concave probe surface shapes and volumes, etc. other than those mentioned or exemplified are expected to be useful.

The words "comprising" and "comprises" as used throughout the claims is interpreted "including but not limited to".

The present invention may suitably comprise, consist or consist essentially of the elements disclosed and may be practiced in the absence of an element not disclosed. For instance, in one non-limiting embodiment, there is provided an under-deposit corrosion sensor consisting essentially of or consisting of a probe body; a curved concave probe surface of constant radius consisting essentially of or consisting of at least one reference electrode surface, at least one working electrode surface, and at least one counter electrode surface, where the respective electrode surfaces are electrically insulated one from each other, and where the under-deposit corrosion sensor further consists essentially of or consists of a porous, electrically insulating layer over the at least one reference electrode surface and the at least one counter electrode surface, which porous, electrically insulating layer conducts ions therethrough, where there is no porous, electrically insulating layer over the at least one working electrode surface; and an electrically conductive lead electrically attached to each respective electrode surface.

In a different non-restrictive version, there may be provided a system for monitoring under-deposit corrosion in real time consisting essentially of or consisting of a structure having a concave, curved bottom surface of radius R, where the structure is selected from the group consisting of a pipeline, a tubing, a conduit, a vessel, a tank, a container and other process equipment and an under-deposit corrosion (UDC) sensor, where the under-deposit corrosion sensor is mounted in the bottom of the structure so that the curved concave probe surface is flush with the concave, curved bottom surface of the structure. The UDC sensor consists essentially of or consists of a probe body; a curved concave probe surface of constant radius R consisting essentially of or consisting of at least one reference electrode surface, at least one working electrode surface, and at least one counter electrode surface, where the respective electrode surfaces are electrically insulated one from each other, and the UDC sensor further consists essentially of or consists of a porous, electrically insulating layer over the at least one reference electrode surface and the at least one counter electrode surface, which porous, electrically insulating layer conducts ions therethrough, where there is no porous, electrically insulating layer over the at least one working electrode surface an electrically conductive lead electrically attached to each respective electrode surface. The system additionally consists essentially of or consists of a machine electrically connected to and configured to receive measurements from the electrically conductive leads, and further configured to measure and/or analyze the measurements for data selected from the group consisting of changes in electrical potential, linear polarization resistance, localized corrosion rate, electrical resistance, electrical charge and combinations thereof.

Alternatively an electrically conductive lead electrically attached to each respective electrode surface, there may be provided a method of measuring under-deposit corrosion, the method consisting essentially of or consisting of utilizing the system for monitoring under-deposit corrosion in real time that is described in the previous paragraph, where the method further consists essentially of or consists of measuring and/or analyzing the measurements for data selected from the group consisting of changes in electrical potential, linear polarization resistance, localized corrosion rate, electrical resistance, electrical charge and combinations thereof.

What is claimed is:

1. An under-deposit corrosion sensor comprising:
    a probe body;
    a curved concave probe surface of constant radius comprising:
        at least one reference electrode surface;
        at least one working electrode surface; and
        at least one counter electrode surface, where the respective electrode surfaces are electrically insulated one from each other;
    a porous, electrically insulating layer over the at least one reference electrode surface and the at least one counter electrode surface, which porous, electrically insulating layer conducts ions therethrough, where there is no porous, electrically insulating layer over the at least one working electrode surface; and
    an electrically conductive lead electrically attached to each respective electrode surface.

2. The under-deposit corrosion sensor of claim 1 where the at least one working electrode surface has a deposit thereon, where the deposit is selected from the group consisting of ferrous sulfide, ferrous oxide, ferrous carbonate, silicate, and combinations thereof.

3. The under-deposit corrosion sensor of claim 2 where the deposit additionally comprises an organic material selected from the group consisting of asphaltenes, paraffins, biofilms, and combinations thereof.

4. The under-deposit corrosion sensor of claim 2 where the deposit has a thickness ranging from about 0.01 mm to about 1 cm.

5. The under-deposit corrosion sensor of claim 1 where the curved concave probe surface has a shape selected from the group consisting of a partial cylinder and a partial sphere.

6. The under-deposit corrosion sensor of claim 1 where the porous, electrically insulating layer is selected from the group consisting of a glass frit, an ionically conductive polymer, ionic crystals, solid electrolytes, and combinations thereof.

7. The under-deposit corrosion sensor of claim 1 where the working electrode surface and the counter electrode surface each have greater area than the reference electrode surface.

8. A system for monitoring under-deposit corrosion in real time comprising:
    a structure having a bottom with a shape selected from the group consisting of a flat surface, a concave, curved bottom surface of radius R, and combinations thereof, where the structure is selected from the group consisting of a pipeline, a tubing, a conduit, a vessel, a tank, a container, and combinations thereof;
    an under-deposit corrosion sensor mounted in the bottom of the structure so that the curved concave probe surface is flush with the concave, curved bottom surface of the structure, where the under-deposit corrosion sensor comprises:

a probe body;
a curved concave probe surface of constant radius R comprising:
at least one reference electrode surface;
at least one working electrode surface; and
at least one counter electrode surface, where the respective electrode surfaces are electrically insulated one from each other;
a porous, electrically insulating layer over the at least one reference electrode surface and the at least one counter electrode surface, which porous, electrically insulating layer conducts ions therethrough, where there is no porous, electrically insulating layer over the at least one working electrode surface; and
an electrically conductive lead electrically attached to each respective electrode surface, and
a machine electrically connected to and configured to receive measurements from the electrically conductive leads, and further configured to measure and/or analyze the measurements for data selected from the group consisting of changes in electrical potential, linear polarization resistance, localized corrosion rate, electrical resistance, electrical charge and combinations thereof.

9. The system of claim 8 where at least the at least one working electrode surface of the under-deposit corrosion sensor has a deposit thereon, where the deposit is selected from the group consisting of ferrous sulfide, ferrous oxide, ferrous carbonate, silicate, and combinations thereof.

10. The system of claim 9 where the deposit on the under-deposit corrosion sensor additionally comprises an organic material selected from the group consisting of asphaltenes, paraffins, biofilms, and combinations thereof.

11. The system of claim 9 where the deposit has a thickness ranging from about 0.01 mm to about 1 cm.

12. The system of claim 8 where the curved concave probe surface of the under-deposit corrosion sensor has a shape selected from the group consisting of a partial cylinder and a partial sphere.

13. The system of claim 8 where in the under-deposit corrosion sensor the porous, electrically insulating layer is selected from the group consisting of a glass frit, an ionically conductive polymer, ionic crystals, solid electrolytes, and combinations thereof.

14. The system of claim 8 where in the under-deposit corrosion sensor the working electrode surface and the counter electrode surface each have greater area than the reference electrode surface.

15. A method of measuring under-deposit corrosion, the method comprising utilizing a system for monitoring under-deposit corrosion in real time comprising:
a structure having a bottom with a shape selected from the group consisting of a flat surface, a concave, curved bottom surface of radius R, and combinations thereof, where the structure is selected from the group consisting of a pipeline, a tubing, a conduit, a vessel, a tank, a container, and combinations thereof;
an under-deposit corrosion sensor mounted in the bottom of the structure so that the curved concave probe surface is flush with the concave, curved bottom surface of the structure, where the under-deposit corrosion sensor comprises:
a probe body;
a curved concave probe surface of constant radius R comprising:
at least one reference electrode surface;
at least one working electrode surface; and
at least one counter electrode surface, where the respective electrode surfaces are electrically insulated one from each other;
a porous, electrically insulating layer over the at least one reference electrode surface and the at least one counter electrode surface, which porous, electrically insulating layer conducts ions therethrough, where there is no porous, electrically insulating layer over the at least one working electrode surface; and
an electrically conductive lead electrically attached to each respective electrode surface, and
a machine electrically connected to and configured to receive measurements from the electrically conductive leads, and further configured to measure and/or analyze the measurements for data selected from the group consisting of changes in electrical potential, linear polarization resistance, localized corrosion rate, electrical resistance, electrical charge and combinations thereof;
where the method further comprises measuring and/or analyzing the measurements for data selected from the group consisting of changes in electrical potential, linear polarization resistance, localized corrosion rate, electrical charge and combinations thereof.

16. The method of claim 15 where method additionally comprises forming on the curved concave probe surface of the under-deposit corrosion sensor a deposit selected from the group consisting of ferrous sulfide, ferrous oxide, ferrous carbonate, silicate, and combinations thereof.

17. The method of claim 16 where the deposit on the under-deposit corrosion sensor additionally comprises an organic material selected from the group consisting of asphaltenes, paraffins, biofilms, and combinations thereof.

18. The method of claim 16 where the deposit has a thickness ranging from about 0.01 mm to about 1 cm.

19. The method of claim 15 further comprising:
introducing a chemical into the structure; and
measuring whether under-deposit corrosion changes after introducing the chemical.

* * * * *